(12) United States Patent
Bronk et al.

(10) Patent No.: US 11,498,752 B2
(45) Date of Patent: Nov. 15, 2022

(54) DIGESTER COVER LEFT-IN-PLACE BALLAST RING

(71) Applicant: Evoqua Water Technologies LLC, Pittsburgh, PA (US)

(72) Inventors: Matthew P. Bronk, Sussex, WI (US); Douglas N. Muller, Green Lane, PA (US); Thomas Mangione, Janesville, WI (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 208 days.

(21) Appl. No.: 15/931,674

(22) Filed: May 14, 2020

(65) Prior Publication Data
US 2021/0094754 A1 Apr. 1, 2021

Related U.S. Application Data

(62) Division of application No. 15/979,660, filed on May 15, 2018, now Pat. No. 10,683,162.

(60) Provisional application No. 62/508,045, filed on May 18, 2017.

(51) Int. Cl.
| | |
|---|---|
| *B21D 53/00* | (2006.01) |
| *B65D 88/40* | (2006.01) |
| *C02F 11/04* | (2006.01) |
| *C02F 3/28* | (2006.01) |
| *C12M 1/107* | (2006.01) |
| *C12M 1/00* | (2006.01) |
| *B22C 9/06* | (2006.01) |

(52) U.S. Cl.
CPC ............. *B65D 88/40* (2013.01); *B21D 53/00* (2013.01); *B22C 9/061* (2013.01); *C02F 3/28* (2013.01); *C02F 11/04* (2013.01); *C12M 21/04* (2013.01); *C12M 23/36* (2013.01); *C12M 23/38* (2013.01); *Y10T 29/49616* (2015.01); *Y10T 29/49623* (2015.01); *Y10T 29/49625* (2015.01); *Y10T 29/49627* (2015.01)

(58) Field of Classification Search
CPC ........ B21D 53/00; C12M 23/38; B65D 88/40; B22C 9/061; Y10T 29/49616; Y10T 29/49623; Y10T 29/49627; Y10T 29/49625
See application file for complete search history.

(56) References Cited

U.S. PATENT DOCUMENTS

| | | |
|---|---|---|
| 3,288,295 A | 11/1966 | Kelly |
| 3,535,236 A | 10/1970 | Travis |
| 3,767,570 A | 10/1973 | Clapp |

(Continued)

*Primary Examiner* — Jermie E Cozart (57) ABSTRACT

A sludge digester including a vessel and floating cover. The vessel includes a sidewall and an interior volume configured to receive and contain sludge. According to one embodiment, the cover comprises a frame structure that is constructed and arranged to form a skirt member formed at a periphery of the cover and extending downwardly into the vessel, and a continuous ballast ring attached to a lower portion of the skirt member and configured to form a trough member with an interior surface of the skirt member. The sludge digester may also include a guide system coupled to the sidewall and the skirt member and configured to allow vertical displacement of the cover with change in volume of at least one of a gas and a sludge contained in the vessel beneath the cover.

5 Claims, 11 Drawing Sheets

(56) References Cited

U.S. PATENT DOCUMENTS

| | | | |
|---|---|---|---|
| 3,894,953 A | 7/1975 | Torpey | |
| 3,976,568 A | 8/1976 | Torpey | |
| 4,391,705 A * | 7/1983 | Cook | C02F 3/28 |
| | | | 435/801 |
| 4,530,762 A | 7/1985 | Love | |
| 4,710,292 A | 12/1987 | DeVos | |
| 4,919,814 A | 4/1990 | Carnahan et al. | |
| 4,940,544 A | 7/1990 | Gode et al. | |
| 5,092,482 A | 3/1992 | Wight | |
| 5,133,875 A | 7/1992 | Carnahan | |
| 5,534,141 A | 7/1996 | McAnaney et al. | |
| 5,540,836 A | 7/1996 | Coyne | |
| 5,545,325 A | 8/1996 | Hsu et al. | |
| 5,702,572 A | 12/1997 | Fujimura et al. | |
| 5,702,604 A | 12/1997 | Yamasaki et al. | |
| 5,741,417 A | 4/1998 | Patzig et al. | |
| 5,861,096 A | 1/1999 | Mason et al. | |
| 5,874,003 A | 2/1999 | Rose | |
| 6,207,059 B1 | 3/2001 | Moore, III | |
| 6,291,232 B1 | 9/2001 | Miller, III | |
| 6,444,124 B1 | 9/2002 | Onyeche et al. | |
| 6,592,755 B1 | 7/2003 | Nurse, Jr. | |
| 6,616,844 B2 | 9/2003 | Park et al. | |
| 6,630,072 B2 | 10/2003 | Hoffland | |
| 6,645,374 B2 | 11/2003 | Cote et al. | |
| 7,087,170 B2 | 8/2006 | You et al. | |
| 7,169,296 B2 | 1/2007 | Humphrey et al. | |
| 7,329,340 B2 | 2/2008 | McWhirter et al. | |
| 7,329,341 B2 | 2/2008 | Yamasaki et al. | |
| 7,435,340 B2 | 10/2008 | Johnson et al. | |
| 7,435,349 B2 | 10/2008 | You et al. | |
| 7,438,817 B2 | 10/2008 | Nagghappan et al. | |
| 7,547,392 B2 | 6/2009 | Gordon | |
| 7,803,272 B2 | 9/2010 | Yamasaki et al. | |
| 8,101,070 B2 | 1/2012 | Theodore et al. | |
| 8,173,419 B2 | 5/2012 | Isaka et al. | |
| 8,372,274 B2 | 2/2013 | Early et al. | |
| 8,562,828 B2 | 10/2013 | Tabata et al. | |
| 8,623,205 B2 | 1/2014 | Woodard | |
| 8,679,314 B1 | 3/2014 | Snyder et al. | |
| 8,764,947 B2 | 7/2014 | Tang et al. | |
| 9,079,125 B2 | 7/2015 | Reilly et al. | |
| 9,120,038 B2 | 9/2015 | Reilly et al. | |
| 9,902,633 B2 | 2/2018 | Reilly et al. | |
| 2007/0256982 A1 | 11/2007 | Kelley et al. | |
| 2007/0272610 A1 | 11/2007 | Isaka et al. | |
| 2008/0164187 A1 | 7/2008 | Sumino et al. | |
| 2008/0164196 A1 | 7/2008 | Sumino et al. | |
| 2008/0190859 A1 | 8/2008 | Stoermann | |
| 2008/0277328 A1 | 11/2008 | Zhao et al. | |
| 2009/0008314 A1 | 1/2009 | Isaka et al. | |
| 2009/0008315 A1 | 1/2009 | Isaka et al. | |
| 2009/0008326 A1 | 1/2009 | Isaka et al. | |
| 2009/0045120 A1 | 2/2009 | Harmon et al. | |
| 2010/0012557 A1 | 1/2010 | Chaffee | |
| 2010/0163473 A1 | 7/2010 | Verink | |
| 2012/0055859 A1 | 3/2012 | Reilly et al. | |

\* cited by examiner

DIGESTER COVER LEFT-IN-PLACE BALLAST RING

CROSS-REFERENCE TO RELATED APPLICATIONS

This application is a division application of and claims priority under 35 U.S.C. 120 to U.S. patent application Ser. No. 15/979,660, filed on May 15, 2018, title DIGESTER COVER LEFT-IN-PLACE BALLAST RING, which issued as U.S. Pat. No. 10,683,162 on Jun. 16, 2020, which claims priority under 35 U.S.C. 119 to U.S. Patent Application No. 62/508,045, filed May 18, 2017, each of which is incorporated herein by reference.

FIELD OF THE DISCLOSURE

Aspects relate generally to covers for sludge digesters, and more specifically to floating covers.

SUMMARY

Aspects and embodiments are directed to a floating cover for a sludge digester. In accordance with an embodiment of the present invention there is provided a sludge digester. The sludge digester comprises a vessel having a sidewall and an interior volume configured to receive and contain sludge and a cover configured to extend over the interior volume of the vessel and seal the interior volume from the atmosphere and trap a gas generated by sludge contained in the vessel. The cover comprises a frame structure constructed and arranged to form: a skirt member formed at a periphery of the cover extending downwardly into the vessel, and a continuous ballast ring attached to a lower portion of the skirt member and configured to form a trough member with an interior surface of the skirt member, and a guide system coupled to the sidewall and the skirt member and configured to allow vertical displacement of the cover with change in volume of at least one of the gas and the sludge contained in the vessel beneath the cover.

In accordance with some aspects of the sludge digester, the trough member has a closed bottom end and an open top end.

In accordance with some aspects of the sludge digester, the trough member includes first and second sidewalls extending from the closed bottom end, one of the first and second sidewalls formed from the interior surface of the skirt member.

In accordance with some aspects of the sludge digester, the frame structure includes a series of frame sections, each frame section forming one of a chord or a curve that connect to each other to define a generally circular outer perimeter of the cover.

In accordance with some aspects of the sludge digester, each curved frame section has concavely curved radially outer and inner walls and each chordal frame section has a concavely curved radially outer wall and a planar inner wall.

In accordance with some aspects of the sludge digester, each frame section includes at least one brace element extending between and coupled to the outer and the inner walls.

In accordance with some aspects of the sludge digester, the trough member is configured to hold a ballast material.

In accordance with some aspects of the sludge digester, the ballast material is a continuous solid concrete ring.

In accordance with some aspects of the sludge digester, the cover further includes a gas dome disposed in the center of the cover and extending axially downward below a lower portion of the skirt member.

In accordance with some aspects of the sludge digester, the frame structure is further constructed and arranged to form a series of radial beams, each radial beam extending from an upper portion of the skirt member to the gas dome.

In accordance with some aspects of the sludge digester, the cover further comprises at least one cover plate attached to the frame structure and configured to extend between adjacent radial beams.

In accordance with some aspects of the sludge digester, the frame structure is constructed from steel.

In accordance with some aspects of the sludge digester, the frame structure further includes an inlet opening for delivering ballast material to the trough member.

In accordance with another embodiment of the present invention there is provided a method of forming a cover of a sludge digester, where the sludge digester has a vessel with an interior volume. The method comprises constructing a series of frame structure sections, each section including an outer wall and an inner wall spaced apart from the outer wall, the outer wall and the inner wall extending vertically from a horizontal base portion to form a trough member, and joining the series of frame structure sections to each other to form a continuous ring, the continuous ring forming a perimeter of the cover and sized to fit within an inner diameter of the vessel.

In accordance with some aspects, the method further includes filling at least a portion of the trough member with ballast material to form a continuous solid ring.

In accordance with some aspects, filling is performed inside the interior volume of the vessel.

In accordance with some aspects, constructing each section includes attaching the horizontal base portion to the outer wall.

In accordance with some aspects, the outer wall is constructed to extend vertically above the inner wall and the method further includes attaching a roof structure to an upper portion of the outer wall.

In accordance with another embodiment of the present invention there is provided a form for constructing a cover for a sludge digester. The form comprises a first metal panel shaped to form a bottom panel and a first side panel of a trough member, the first side panel configured to form one of a curved shape or a planar shape, the trough member sized and shaped to be and to hold a continuous ring of ballast material and to connect to a periphery of the cover.

In accordance with some aspects, the form further includes a second metal panel attached to the bottom panel, the second panel forming a second side panel of the trough member and configured to form a curved shape.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Wastewater treatment processes use digestion tanks for anaerobically treating wastewater sludge. During the anaerobic process, gas, a mixture of primarily methane and carbon dioxide, is given off and collected to be used as fuel for performing treatment processes in the system, such as heating the sludge mixture. Some systems employ a floating gas holder positioned above the sludge which collects the gas and provides a controllable downward force on the gas, which results in the gas being pressurized and useable as fuel.

Conventional floating covers are constructed on-site from steel and concrete materials. One of two construction and assembly methods are typically used. The first involves use of separate concrete ballast blocks that are manufactured off-site, delivered, and then lifted individually into the digester tank and positioned on a steel structure that forms the cover. The second involves use of a temporary form that is constructed on-site. Concrete is poured into the temporary form, and once cured, functions as the ballast for the cover.

The use of separate concrete ballast blocks creates several potential problems. One is the potential for the blocks to fall into the digester as the cover ages and the materials deteriorate. Another is that the separate ballast blocks pose a safety risk during the installation phase of the system. Cranes are used to lift the blocks, which can weigh several tons, and place them onto the steel structure inside the digester that is intended to hold them. This requires workers to be in the tank during lifting, since the crane operator is unable to see the blocks once they are lowered into the digester. This creates a "blind lift" operation, which poses safety risks for the workers in the tank.

The use of temporary forms built on-site for forming ballast structures also presents several problems. One is that the temporary formwork is constructed from plywood and has to be built on-site, and in some instances, built inside the digester. The temporary plywood form also has to be built to specified dimensions that may differ from one site to another. The form has to be re-built when these dimensions are not implemented correctly. Once the concrete cures, the forms also have to be removed, and are thrown away as waste. The on-site form-making process thus makes for difficult work and is time consuming.

In accordance with certain embodiments, the use of a continuous ballast ring is used for a floating digester cover. The continuous ballast ring includes ballast material that forms a single structure that can be constructed from concrete and is poured in one operation. The ballast material for the ballast ring therefore does not have any seams or gaps. The continuous ballast ring provides advantages over the use of separate ballast blocks in that it provides rigidity to the cover and minimizes the potential of concrete falling into the digester as the ballast materials deteriorate. The risk to operators inside the tank during the installation phase is also reduced since the ballast material can be delivered and cured within the digester itself.

According to some embodiments, a ballast ring, also referred to as a "ballast pick-up ring" for use in a floating digester cover is configured to provide additional weight to meet desired operating pressures and to allow operation of pressure/vacuum relief safety valves when the digester cover is filled with gas. The ballast ring of the present invention in some embodiments is constructed from a steel form that is designed and fabricated with the digester cover. The steel form is designed to attach to a rim skirt of the digester cover, which allows the installing contractor to fill the form with flowable fill concrete. The steel ballast ring is therefore integral to the rim skirt and is erected with the rim skirt and left in place after being filled with concrete or other ballast material. The steel form provides additional structure to the digester cover, produces a consistent and precise result since it can be designed with optimum dimensions prior to installation, reduces the amount of time needed for an installing contractor to erect the cover, and provides a safer work environment for the installation crew. The steel form also saves time on dismantling and disposing of the temporary concrete formwork that is used in conventional processes.

Figure 1:
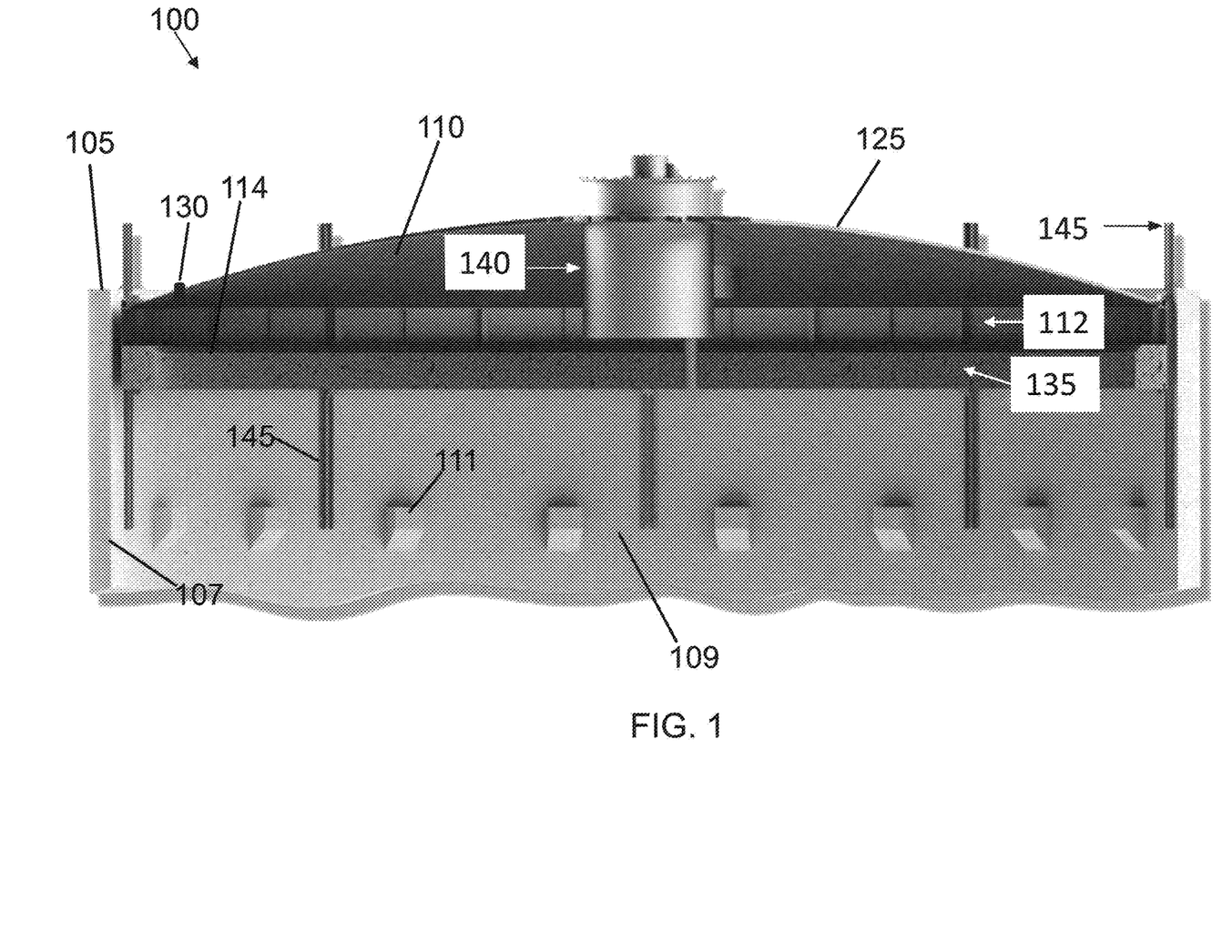
FIG. 1 is a partial schematic and cross-sectional view of a sludge digester with a cover.
Figure 2:
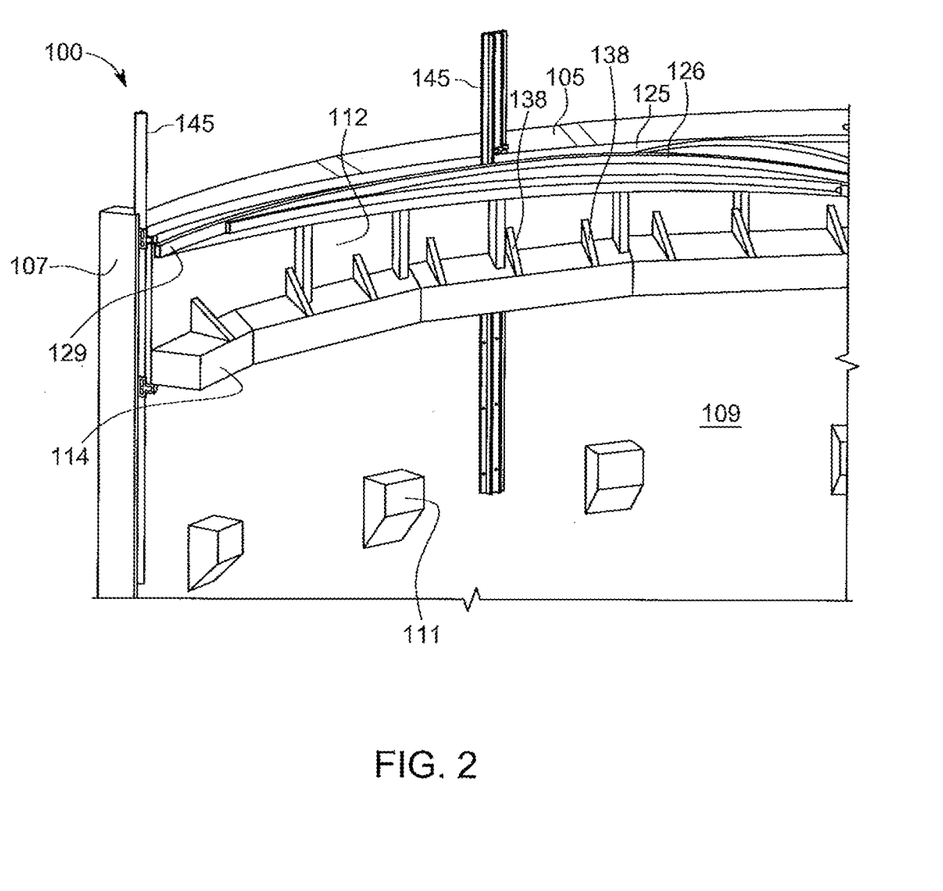
FIG. 2 is an enlarged and partially exploded perspective view of the sludge digester shown in FIG. 1.

Referring to FIGS. 1 and 2, a sludge digester, generally indicated at 100 is shown. The sludge digester 100 includes a vessel 105 having a sidewall 107 and an interior volume 109. A cover 110 includes a skirt member 112 and a continuous ballast ring 114 comprising ballast material 135, such as concrete, is attached to the skirt member 112. The sludge digester 100 also includes a guide system 145 coupled to the sidewall 107 and the skirt member 112 that is configured to allow vertical displacement of the cover 110 with change in volume of at least one of gas and sludge contained in the vessel 105 and beneath the cover 110. The vessel 105 also includes a series of corbels 111 that project inwardly toward the center of the interior volume 109 of the vessel 105. Initially, the operating pressure of the digester is such that a portion of the skirt member 112 and ballast ring are submerged in the sludge and rest on the corbels 111, which may be sized to be wider than the ballast ring. One or more hanger straps 138 may be used to attach the ballast ring 114 to the skirt member 112. The cover 110 may also include a roof structure 125 that attaches to an upper portion of the skirt member 112. The ballast ring 114 shown in FIGS. 1 and 2 does not show the steel ballast form that is described in further detail below.

According to one embodiment, a cover 110 is disclosed that is configured to extend over the interior volume 109 of the vessel 105 and seal the interior volume 109 from the atmosphere and trap gas generated by sludge contained in the vessel 105. One example of a portion of a cover 110 is shown in the cross-sectional view shown in FIG. 3. The cover 110 includes a frame structure 115 that is constructed and arranged to form a skirt member 112, also referred to as a "rim skirt" or "side skirt," and a continuous ballast ring 114 attached to a lower portion of the rim skirt 112. The skirt member 112 is formed at a periphery of the cover and extends downwardly into the vessel 105. The continuous ballast ring 114 is configured to form a trough member 116 with an interior surface 113 of the skirt member 112, an enlarged view of which is shown in FIG. 4.

The trough member 116 may be constructed from one or more pieces of metal material, such as steel (e.g., sheet steel), and includes a closed bottom end or base portion 119, and first and second sidewalls extending from the closed bottom end 119, where one of the first and second sidewalls is formed from the interior surface 113 of the skirt member 112. The other sidewall of the tough member 116 is formed by inner wall 118. The skirt member 112 therefore forms an outer wall of the trough member 116 and the inner wall 118 is spaced apart from the outer wall, with both the inner wall and outer wall extending vertically from the horizontal base portion 119. The frame structure 115 may also include at least one brace element 132 that extends between and is coupled to the outer wall 112 and inner wall 118 of the trough member 116.

Figure 3:
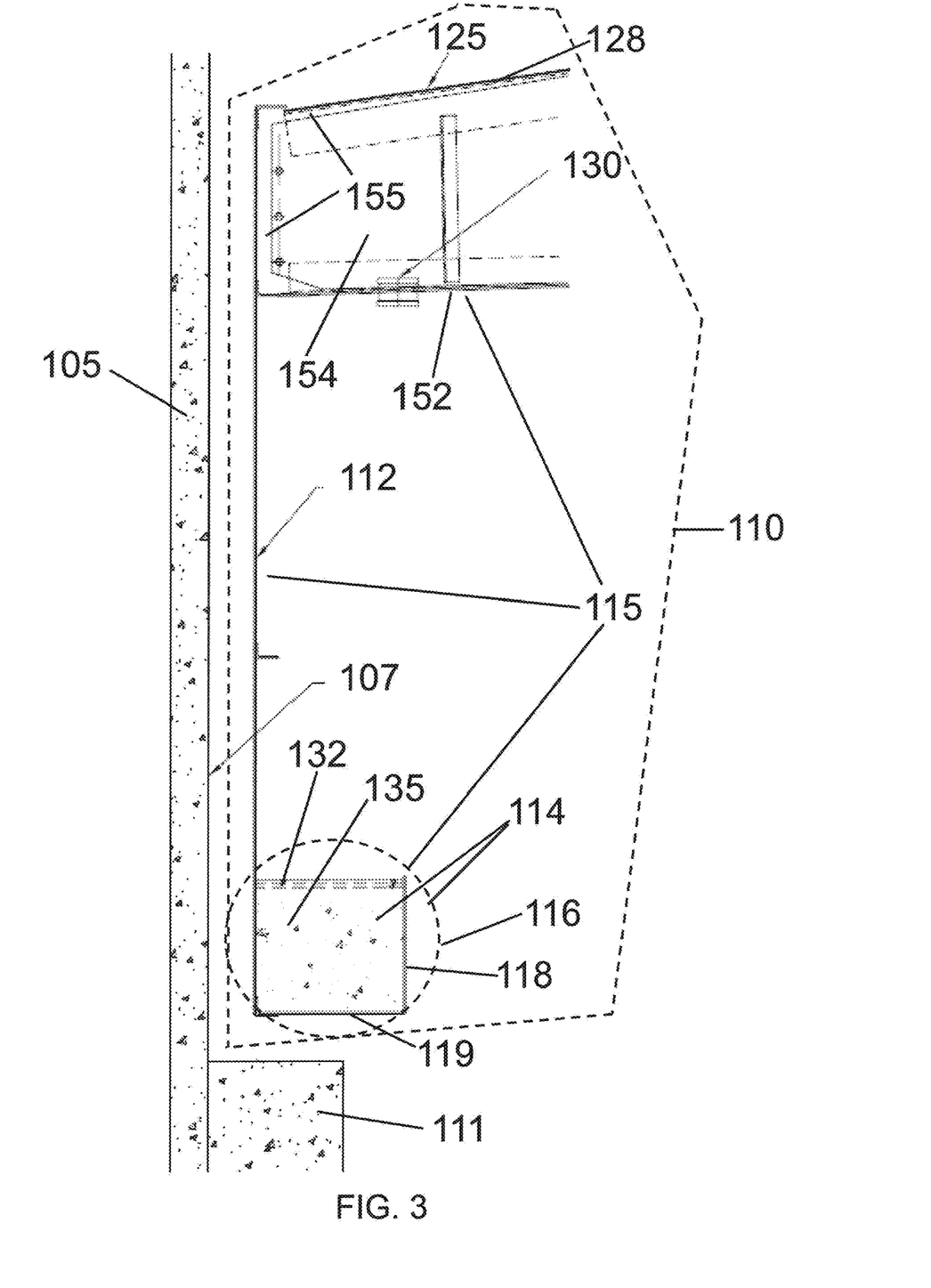
FIG. 3 is a cross-sectional view of an example of a portion of a cover positioned within a vessel of a sludge digester in accordance with aspects of the invention.

As shown in FIG. 3, the trough member 116 is configured to hold a ballast material 135. Non-limiting examples of ballast materials include dense heavy materials such as concrete. Examples of concrete that may be suitable for ballast materials as described herein include concrete having a nominal compressive strength of about 2500 psi to about 4000 psi, when cured. In some embodiments, the ballast material 135 may be concrete having a compressive strength of about 4000 psi. Concrete material can be poured into the trough member 116 once sections 120 of the frame structure 115 have been connected to each other (described in further detail below). When cured, the concrete forms a continuous solid concrete ring.

Figure 4:
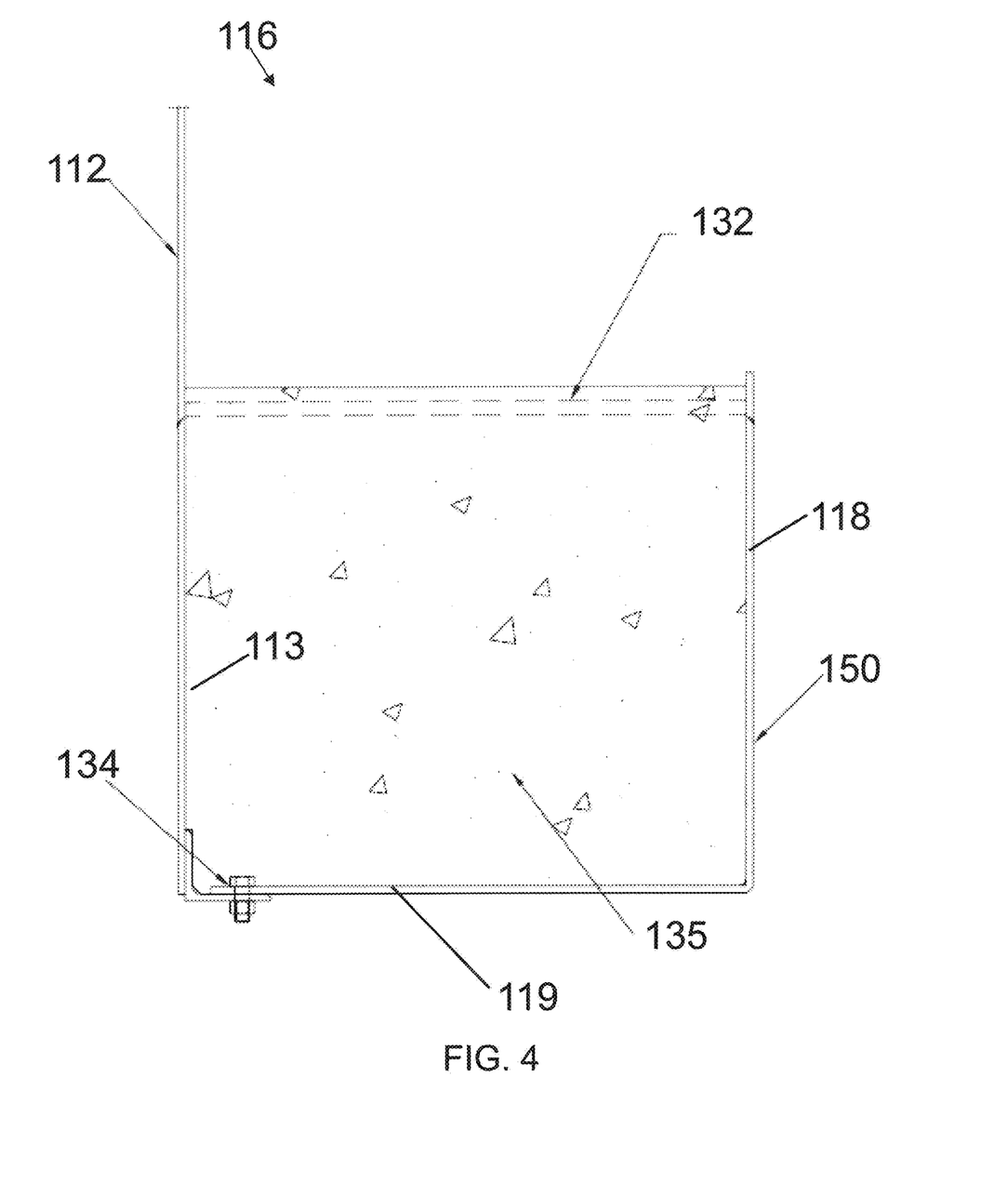
FIG. 4 is an enlarged view of a trough member portion of the cover shown in FIG. 3.
Figure 5:
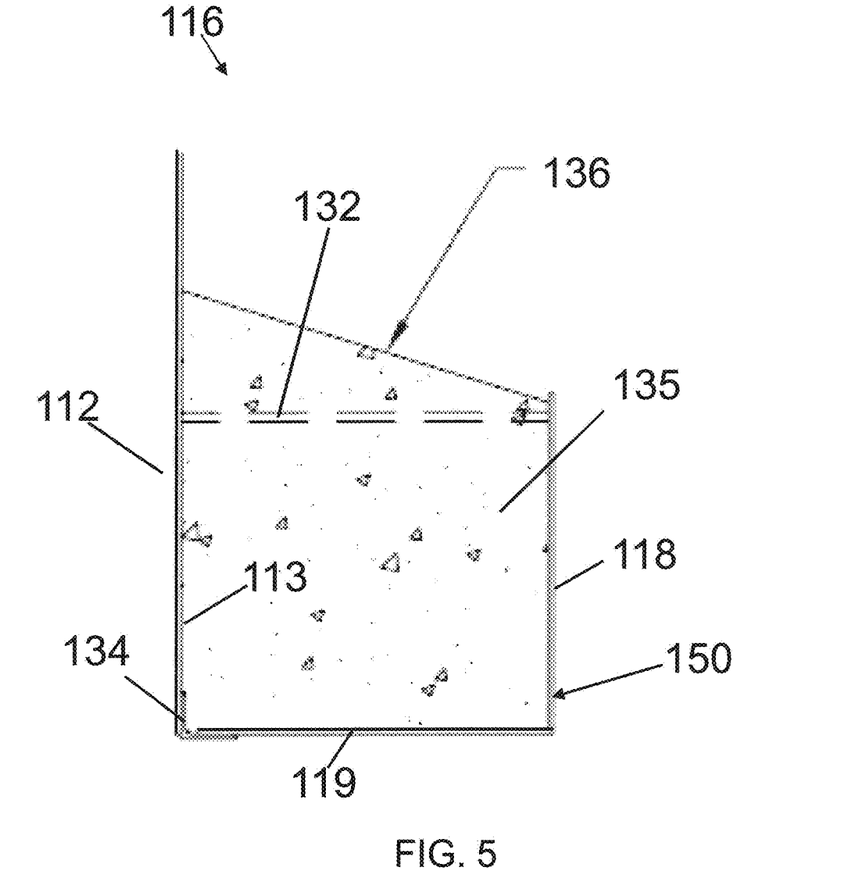
FIG. 5 is a cross-sectional view of an example of a trough member in accordance with aspects of the invention.

FIGS. 4 and 5 show examples of two cross-sectional views of trough member 116. The trough member 116 may be constructed in part from a form 150. According to one embodiment, the form 150 is constructed from a metal panel or sheet that is shaped to form the bottom panel 119 and a first side panel 118 (i.e., inner wall) of the trough member 116. The examples shown in FIGS. 4 and 5 shows the metal panel being a single metal panel, but in other embodiments, the base portion 119 and first side panel 118 may be formed from separate metal panels and then joined together via an attachment mechanism (e.g., welding).

As discussed further below, the frame structure 115, including the trough member 116 of the ballast ring 114, may be formed from metal materials such as steel, including stainless steel, but other materials are also within the scope of this disclosure, including composite materials such as fiber reinforced polymer (FRP) materials. For instance, various types of fibers, including glass, carbon, nylon, polyester, and/or Kevlar® can be included in a polymer matrix to form structural members as described herein.

The form 150 may be attached to the skirt member 112 using an attachment mechanism 134. In the examples shown in FIGS. 4 and 5, the horizontal base portion 119 is attached to the skirt member 112. In one embodiment, the attachment mechanism 134 includes one or more mechanical fasteners, such as bolts, gaskets, screws, washers, rivets and the like. The attachment mechanism 134 shown in FIGS. 4 and 5 is a mechanical type of fastener. In another embodiment, the attachment mechanism 134 is accomplished via welding, e.g., a welded seam or other welded attachment configuration. Welding can be performed on-site or in off-site, depending on the part of the frame structure being constructed and the size of the overall structure. In some instances, both a mechanical fastener and welding techniques may be used for joining portions of the frame structure 115. Once attached, the form 150 includes the metal panel of the skirt member 112, which extends from the bottom panel 119 and forms a second side panel with the first side panel (118) for confining and forming the shape of the ballast material 135.

According to one embodiment, the trough member 116 has an open top end. The top end is disposed opposite the closed bottom end 119 and may be configured to be open for purposes of introducing ballast material 135 to the trough member 116. The closed bottom end 119, inner wall 118, and portion of the interior 113 of the skirt member 112 that comprise the trough member 116 provide rigid support to uncured, pourable, fluid-like ballast material 135 while the ballast material cures into a dense, solid material. The "openness" of the top end of the trough member 116 may be "broken" up by brace elements 132. The brace elements 132 may be formed from a rod-like metal material, such as rebar. In some embodiments, the brace elements 132 extend between and are attached to the skirt member 112 and inner wall 118. In other embodiments, the brace element 132 may extend between the skirt member 112 and inner wall 118 but may not be attached to either structure. The brace elements 132 may provide structural support to the trough member 116 and/or ballast material 135. In some embodiments, the ballast material 135 may be configured to have a sloped top 136, as shown in FIG. 5. In certain instances the sloped top 136 can be formed after the ballast material 135 has been poured and has started to cure or otherwise "set" such that workers can use a temporary form or manually form with a trowel the final sloped shape. The sloped top 136 of the ballast material 135 may function to allow the cover 110 to more easily move vertically (i.e., "rise") through sludge contained in the interior volume 109 of the vessel 105 than a ballast material top that is configured to be horizontally planar. The sloped top 136 may also function to allow runoff of sludge from the ballast ring, which may reduce the rate of deterioration or wear of the ballast material 135.

Figure 6:
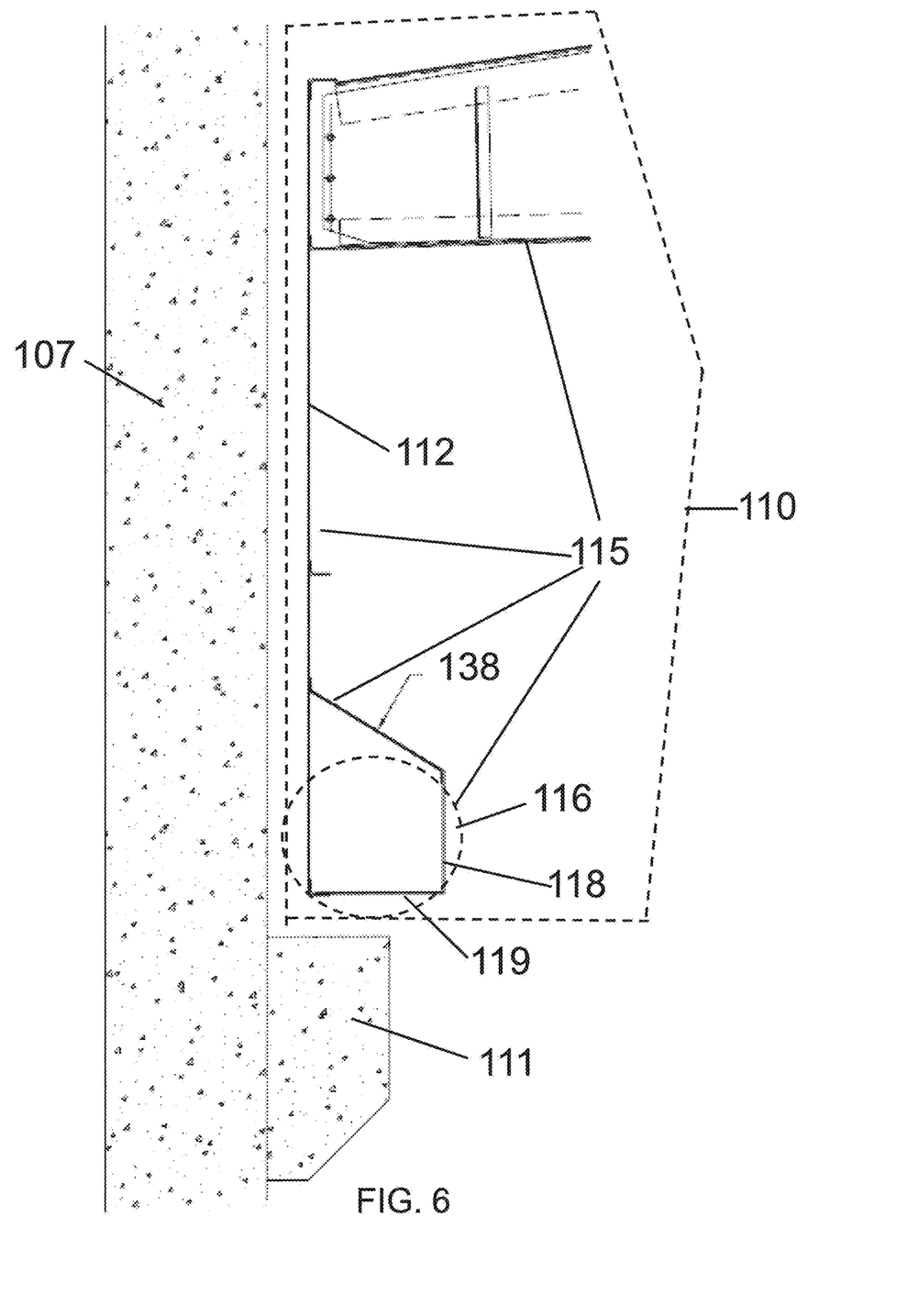
FIG. 6 is a cross-sectional view of another example of a portion of a cover positioned within a vessel of a sludge digester in accordance with aspects of the invention.

Referring now to FIG. 6 another cross-sectional view of the cover 110 is shown. In this view, a hanger strap 138 extends from the skirt member 112 to the inner wall 118 of the trough member 116, which in this particular view does not include ballast material. The hanger strap 138 functions to add structural support to the frame structure 115 and forms another means of attachment for the trough form 150 to attach to the skirt member 112.

Figure 7A:
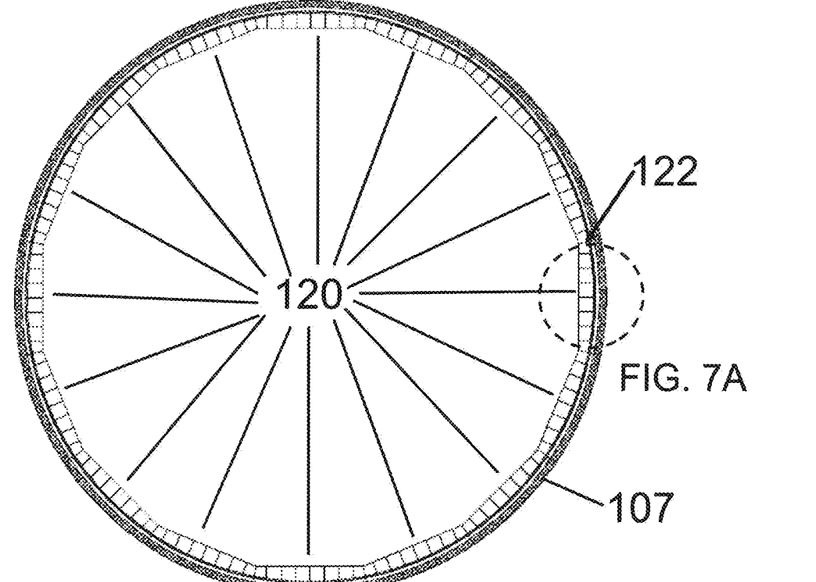
FIG. 7A is a top view of one example of a frame structure for a cover in accordance with aspects of the invention.
Figure 7B:
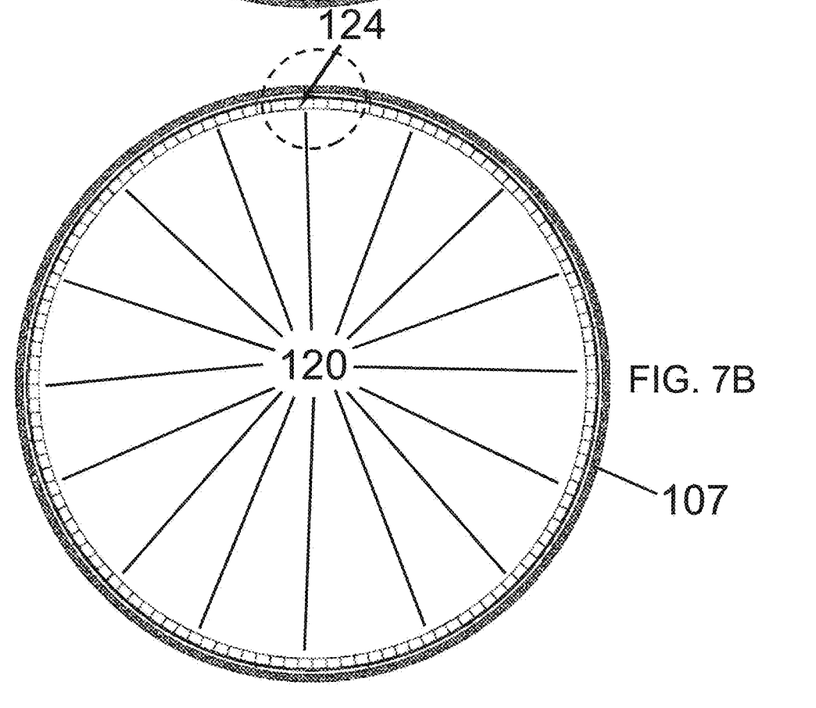
FIG. 7B is a top view of another example of a frame structure for a cover in accordance with aspects of the invention.
Figure 8:
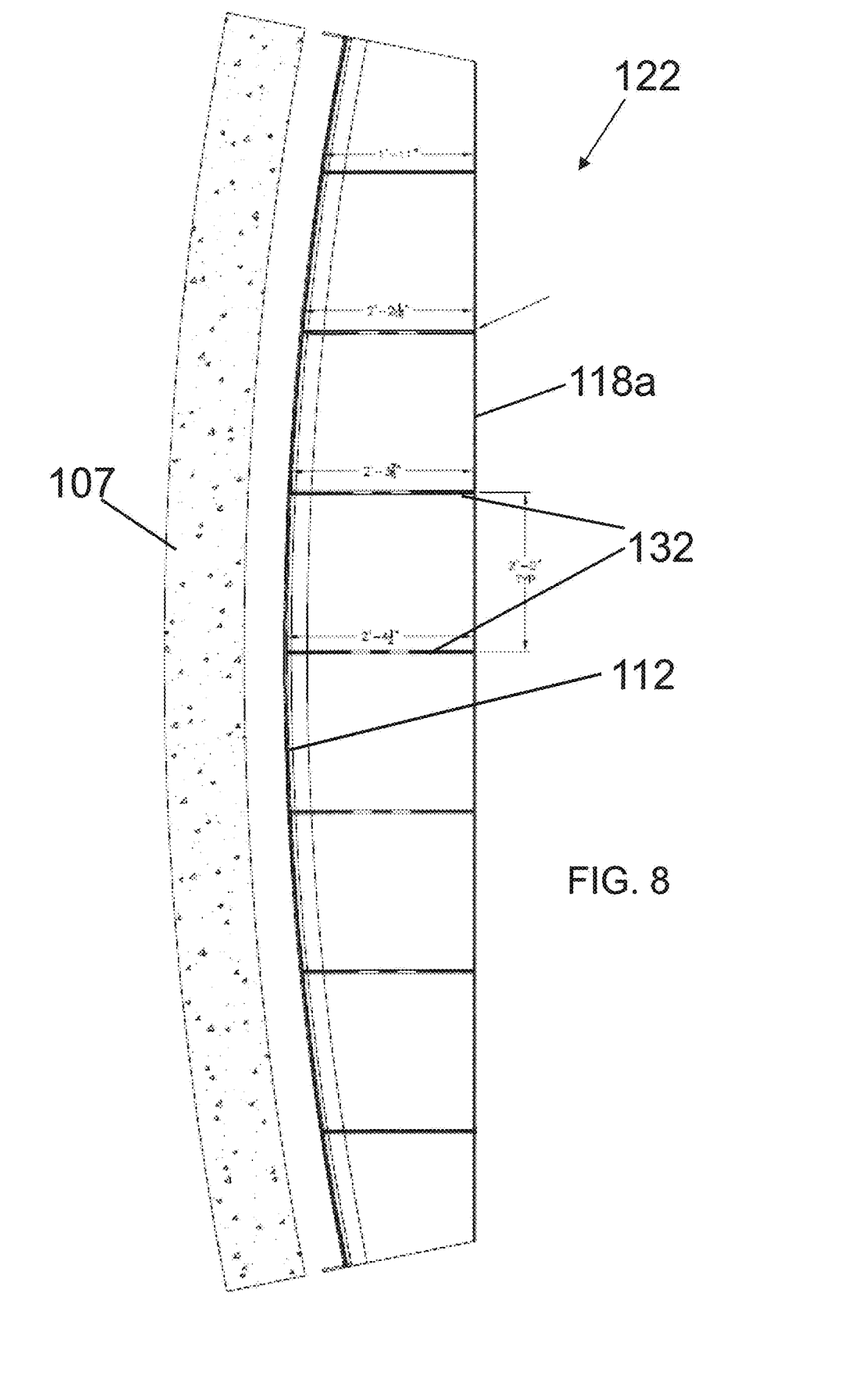
FIG. 8 is a top view of a section of the frame structure shown in FIG. 7A.

The frame structure 115 includes a series of frame sections 120, as shown in the top views of FIGS. 7A and 7B. Each frame section 120 is constructed identically or near-identically and is configured to attach to another frame structure section 120. Each frame structure section 120 (also referred to herein as simply "frame section" or "section") is configured to form one of a chord (e.g., FIG. 7A) or a curve (e.g., FIG. 7B) that connect to each other to define a generally circular outer perimeter of the cover 110. The outer perimeter of the cover is sized to fit within an inner diameter of the sidewall 107 of the vessel 105. According to the examples shown in FIGS. 7A and 7B, 16 frame structure sections 120 are joined together to form the outer perimeter of the cover. It is to be appreciated that other embodiments may include less than or more than 16 frame structure sections, with the number of frame structure sections depending on the specific application, the size of the digester, and the desired dimensions of the ballast ring. In FIG. 7A, each frame structure section 120 forms a chord, and FIG. 8 is a top view of one chordal section 122. The chordal frame section 122 is configured to have a concavely curved radially outer wall 112 (i.e., skirt member 112) and a planar inner wall 118a. Each chordal section 122 also includes brace elements 132 that are spaced at regular intervals and extend between the outer wall 112 and inner wall 118a. As noted above, the example shown in FIG. 7A includes 16 chordal frame sections 122, but it is to be appreciated that the frame structure may be divided into other numbers of chordal sections that are less than or greater than 16. The chordal sections (and curved sections described below) may be sized and shaped such that when they are joined together the outer perimeter of the structure forms a continuous ring that fits within the interior diameter of the vessel.

Figure 9:
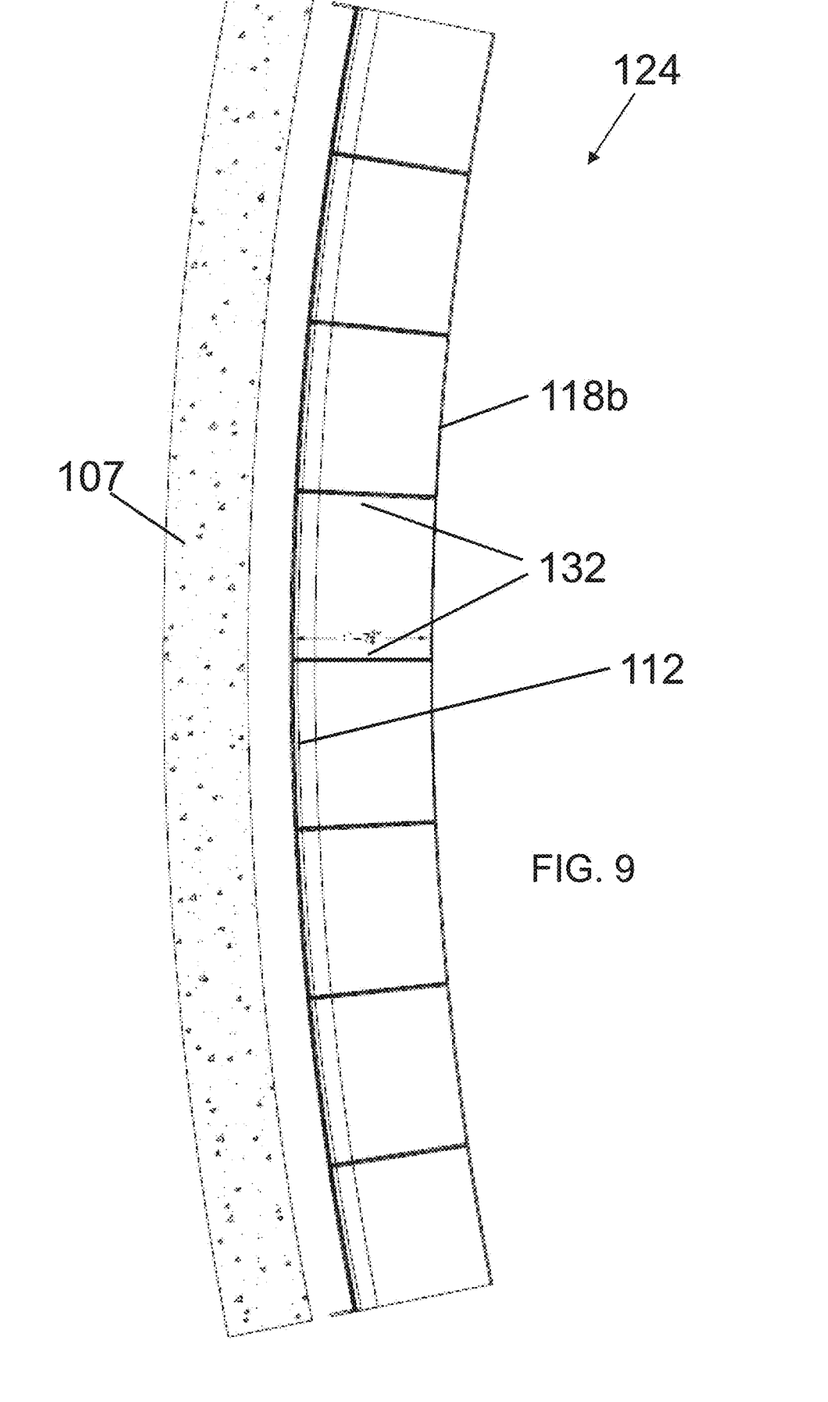
FIG. 9 is a top view of a section of the frame structure shown in FIG. 7B.

In FIG. 7B, each frame structure section 120 forms a curve, and FIG. 9 is a top view of one curved section 124. The curved frame section 124 is configured to have a concavely curved radially outer wall 112 (i.e., skirt member 112) and a concavely curved radially inner wall 118b. Each curved section 124 also includes brace elements 132 that are spaced at regular intervals and extend between the outer wall 112 and the inner wall 118b. The curve of the skirt member 112 and the inner wall 118b may be configured such that the distance between the skirt member 112 and the inner wall 118b is maintained at an even space (i.e., the same distance apart).

As shown in FIGS. 8 and 9, the skirt member 112 that forms the outer wall of each frame structure section 120 is configured to follow the contour of the curve of the interior of the sidewall 107 of the vessel 105. In some embodiments, the skirt member 112 may be spaced apart from the sidewall 107 by a predetermined distance to allow the cover 110 to freely move vertically within the vessel 105 as sludge is introduced to and contained in the vessel 105 and gas is generated from the sludge during the digestion process.

The individual frame structure sections 120 may be joined to each other using any one of a number of different methods. According to one embodiment, the sections 120 are joined using welding techniques. In other embodiments, the sections are joined using mechanical attachment methods, such as bolts and gaskets. In some instances, each section 120 is constructed outside of the interior volume 109 of the vessel 105, and joining the series of frame structure sections 120 is performed inside the interior volume 109 of the vessel 105. For example, the trough form 150 and skirt member 112 may be prefabricated either on-site or off-site. Likewise, the trough form 150 may be attached to the skirt member 112 either off-site or on-site. As attached, these two components of the frame structure 115 may form each frame structure section 120, which may then be individually placed into the vessel 105 where they are then joined together to form a continuous ring. In some instances, the frame structure sections may be joined together outside the vessel, and then lowered in via a crane.

According to one embodiment, the frame structure 115 may be constructed from one or more metal materials such as steel (e.g., carbon steel), including stainless steel, and in some instances may be constructed from aluminum. In other embodiments the frame structure 115 may be constructed from one or more other types of materials, such as composite materials, including carbon reinforced metal composites or other type of composites such as FRP materials. The material or materials used to form the frame structure 115 may be any material that is suitable for meeting the structural and mechanical requirements of the cover and capable of withstanding the environmental conditions experienced by the cover. The frame structure 115 may include panels or sheets of metal material, as well beams, bars, rods, or any other structural element that functions to provide a frame structure as described herein. The frame structure 115 may also include attachment mechanisms, such as attachment mechanism 134 that is used to attach the trough form 150 to the skirt member 112, as well as other attachment mechanisms disposed at joining locations of the structure.

The specific dimensions, e.g., length, width, thickness of material forming the frame structure 115, depend on the specific application and/or dimensions of the vessel. In some embodiments, the panels forming the skirt member 112 and trough form 150 are constructed from steel that is at least ¼ inch thick. The thickness of the steel may depend on the particular design and may be as thick as deemed necessary to comply with the structural and mechanical requirements of the cover. According to some embodiments, the brace elements 132 are formed from metal rod material having a ½ inch diameter.

In certain embodiments, the trough member 116 is sized or otherwise configured to accommodate expansion and contraction of the ballast material 135 and/or frame structure material. For instance, joints where mating pieces or sections of frame structure meet may include channels, gaps, or an elastic material to allow adjoining materials to expand or contract. These joints may be hermetically sealed via other structural portions of the joint.

According to some embodiments, the trough form 150 is configured to attach to a lower portion of the skirt member 112. Positioning the ballast at a lower portion of the skirt member 112 functions to lower the metacenter of the cover, as well as add stability to the cover. In some embodiments, the bottom end 119 of the form 150 aligns with the bottom edge of the skirt member 112, as shown in FIGS. 4 and 5. This configuration allows for at least a portion of the bottom end 119 of the trough member 116 to "rest" on the corbel structures 111. The examples shown in the figures include individual corbels 111, but it is to be appreciated that the corbels may be constructed as a continuous structure that forms a support "shelf" around the interior of the vessel sidewall 107. In some embodiments, the bottom end 119 of the trough form 150 may attach further up from the bottom edge of the skirt member 112, such that a "lip" of the skirt member 112 extends down below the bottom end 119.

As described above, the frame structure 115 comprises the skirt member 112 and the ballast ring 114. The trough form 150 of the continuous ballast ring 114 is not removed once the ballast material 135 is added and therefore contributes to the weight of the ballast ring 114. Gas produced by the sludge contained in the vessel 105 is pressurized by the weight of the cover, including the ballast ring 114. The pressurized gas can then be removed via the gas dome 140 and/or safety valve 148 (see FIG. 10 for example of safety valve 148).

In one embodiment, the frame structure 115 includes one or more inlet openings for delivering ballast material 135 to the trough member 116 inside the vessel. The inlet opening(s) may function to provide a connection for fill hoses that are used to deliver ballast material to the trough member 116. The inlet opening(s) may provide structural support for the fill hoses and also allow for maneuverability within the vessel 105 during the filling process. One example of such an inlet opening is shown in FIG. 3 at 130. The inlet opening 130 may be positioned at one or more locations in the frame structure 115. The example shown in FIG. 3 has the inlet opening 130 formed within a ceiling plate 152 of the roof structure 125 (described in further detail below). In this position, one or more fill hoses can be connected to this location (e.g., a top threaded portion of the inlet opening 130) from the concrete delivery vehicle, and then one or more additional fill hoses can be attached to the inlet opening (e.g., a bottom threaded portion of the inlet opening 130) that can be used for targeted delivery to the trough member 116. Additional inlet openings may be formed in other locations, for instance in the cover plate 128 of the roof structure shown in FIG. 3.

In accordance with at least one embodiment, the frame structure 115 further includes a roof structure 125. The roof structure 125 is configured to keep atmospheric air from entering the digester and mixing with the generated biogas. In some embodiments, the roof structure 125 is attached to an upper portion of the skirt member 112, which extends vertically above the inner wall 118 of the trough member 116.

Figure 10:
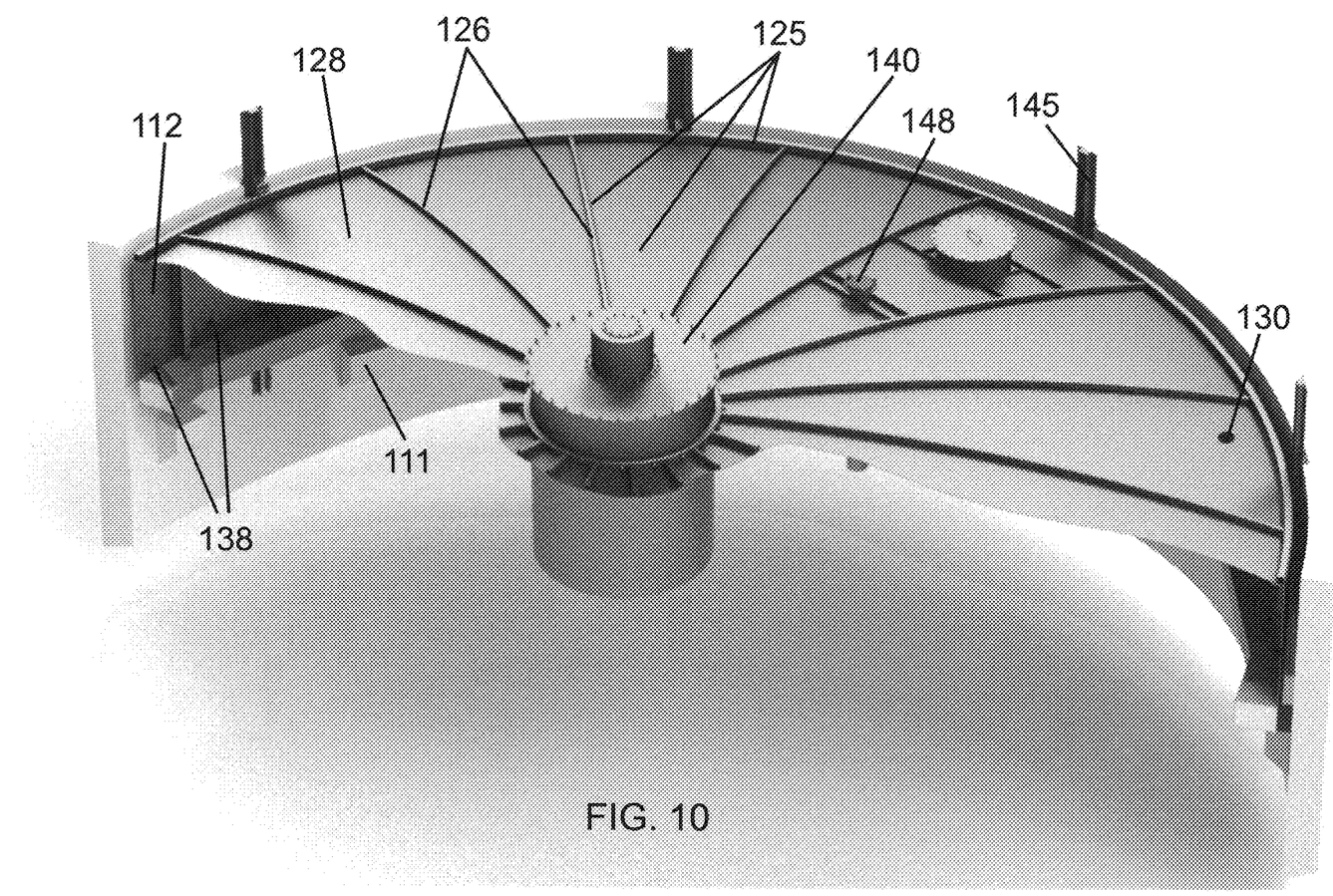
FIG. 10 is a top perspective view of the sludge digester shown in FIG. 1.
Figure 11:
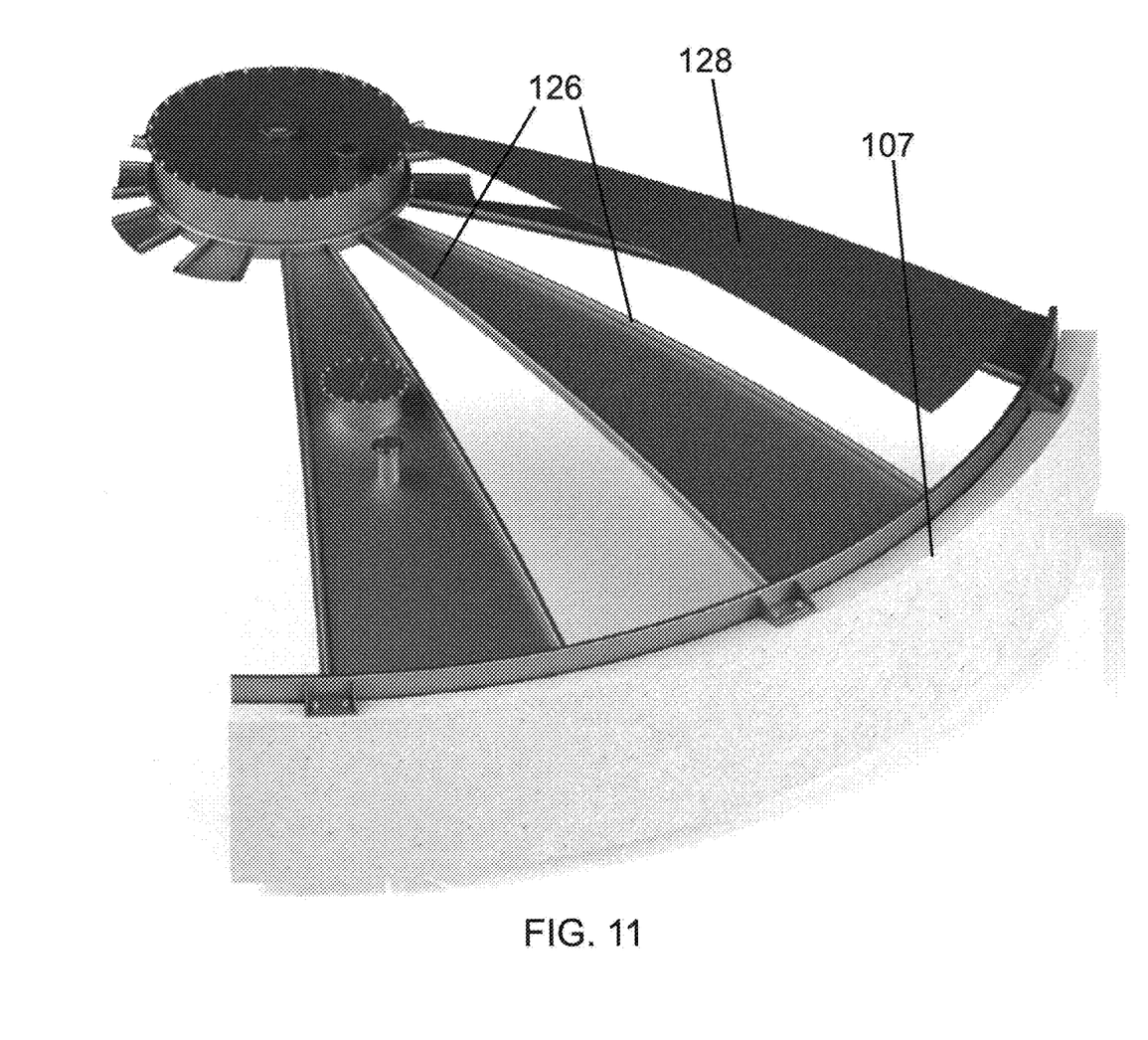
FIG. 11 is an enlarged and partially exploded perspective view of the structure shown in FIG. 10, with portions removed.

One non-limiting example of a roof structure 125 is shown in FIGS. 10 and 11. For example, a series of radial beams 126, as shown in FIGS. 10 and 11, extend from an upper portion of the skirt member 112 to the gas dome 140 disposed in the center of the cover 110. The radial beams 126 may curve upward into an arc or arch, which increases the volume of space beneath the cover for storing gas generated by the sludge. One or more cover plates 128 attach to the frame structure 115 and are configured to extend between adjacent radial beams 126. In some instances, a single cover plate 128 may be used that is attached to an underside (or alternatively, a top side) of the radial beams 126. As shown in FIG. 2, according to some embodiments, the upper portion of the skirt member 112 may be attached to a peripheral structure 129 (also referred to as an outer thrust ring) that extends around the top perimeter of the cover 110. For instance, the example shown in FIG. 2 includes a skirt member 112 where the upper edge is bent to form a "shelf" that is attached to the peripheral structure 129. As indicated in FIG. 2, the radial beams 126 may attach to the peripheral structure 129. The peripheral structure 129 may be constructed from the same material as the frame structure 115, such as steel, and may be configured to ensure that no excessive loading is transferred to the sidewall 107 of the vessel 105. This may allow for the cover 110 to more easily move vertically within the vessel 105. One or more of the cover plates 128 may include an inlet opening 130, as indicated in FIGS. 1 and 10, for assisting in delivering ballast material.

Another example style of roof structure 125 is shown in FIG. 3 (and FIG. 6, although not explicitly labeled) which includes a truss style roof. As shown in FIG. 3, roof trusses 155 form a structural frame for the roof structure. Cover plates 128 and ceiling plates 152 attach to the top and bottom of the trusses 155 respectively, with an air space or attic space 154 formed in between the cover plates 128 and ceiling plates 152. The attic space 154 may function to protect the roof trusses 155 from corrosion and may also provide insulation for the sludge contained in the vessel.

Other types of roof structures are also within the scope of this disclosure. In addition, other structural elements may also be included in the roof structure, such as purlins that connect between the main structural beams/ribs and add lateral bracing, rigidity and support.

According to at least one embodiment, the form 150 may be attached to the skirt member 112 to form a frame structure section 120, and then the frame structure sections 120 may be attached to each other. The roof structure 125 may then be attached to the joined frame structure sections. For instance, the radial beams 126 may be attached to the skirt member 112 after the frame structure sections 120 are positioned and joined to one another. The cover plate(s) 128 may be added after the radial beams 126 are attached to the skirt member 112.

Depending on the size of the cover, one or more portions of the frame structure 115 may be formed inside or outside the vessel 105. For instance, in some instances, the frame structure sections 120 may be attached to one another and the roof structure 125 attached to the frame structure sections 120 external to the vessel 105. Then the entire frame structure 115 may be lowered into the vessel via a crane, and once inside the vessel 105, the ballast material 135 may be delivered to the form 150. In other instances, the frame structure sections 120 may be constructed external to the vessel and then attached to each other inside the vessel. The roof structure 125 may then be attached.

According to some embodiments, the gas dome 140 is configured to form a liquid seal with the sludge contained in the vessel 105, which traps gas produced by the sludge and contributes to the ability of the cover 110 to float. For example, the gas dome 140 is disposed in the center of the cover 110 and may extend axially downward below a lower portion of the skirt member 112. The ballast ring 114 formed from the trough member 116 and ballast material 135 is initially submerged within sludge contained in the vessel 105. As the volume of gas generated from the digesting sludge increases, a buoyant force is exerted by the sludge upon the ballast ring 114 according to Archimedes principal. The ballast ring 114 begins to rise through the sludge, and eventually "floats" on a surface of the sludge such that the ballast ring 114 is partially submerged during normal operation. The pressure relief or safety valve 148 is configured such that the gas pressure under the cover 110 does not exceed the static weight of the cover 110. Keeping the gas pressure below this threshold gas pressure allows for the ballast ring 114 to remain partially submerged, which adds to the stability of the cover 110. If the threshold gas pressure under the cover is exceeded, the ballast ring 114 becomes unsubmerged and floats, which makes the cover 110 unstable and may allow for gas contained under the cover to escape to the atmosphere.

When concrete is used as the ballast material 135, the concrete typically has a density of about 150 pounds per cubic foot. A cubic foot of concrete in a submerged condition in sludge having a specific gravity of about 1.0 has an effective weight which is reduced by the weight of a cubic foot of sludge (about 62.4 pounds per cubic foot). Thus, in a submerged condition, one cubic foot of solid concrete ballast exerts a downward force of about 87.6 pounds. The weight of the form 150 may also be factored into this calculation, but the weight of the form is negligible when compared with the weight of the ballast material.

When the ballast ring 114 emerges from the sludge, the effective weight of the concrete is its normal density, i.e., about 150 lbs/ft$^3$. Thus, the total weight of the cover is significantly greater when the ballast members are in an emerged condition than when the ballast members are in a submerged condition. This creates a gas pressure differential between the submerged and emerged positions of the ballast. Typically, the operating pressure of the digester is that of the ballast when it is raised from the corbels but still in a submerged condition. When the ballast ring 114 fully emerges from the sludge, the pressure generated is usually at or above the relief valve settings so that typically the ballast ring 114 is never fully emerged from the sludge without the relief valves on the cover relieving the pressure of the gas. The ballast ring 114 is therefore sized to provide the required dead weight to meet the desired operating pressure. The ballast ring 114 may also be sized based on a desired increase in pressure (threshold pressure) that occurs from the ballast becoming unsubmerged.

Referring back to FIGS. 1 and 2, the sludge digester 100 according to at least one embodiment also includes a guide system 145. In some embodiments, the guide system 145 is coupled to the sidewall 107 of the vessel 105. The floating cover 110 has a high center of gravity and is mainly supported on gas generated by the digesting sludge contained in the vessel. These factors make the cover 110 unstable, and therefore the guide system 145 may not only function to allow vertical displacement of the cover 110, but may also function to provide stability to the cover 110 throughout its range of travel. The example shown in FIGS. 1 and 2 is configured as a vertical guide system 145, but other configurations are also within the scope of this disclosure, such as spiral guide systems. The guide system 145 may include a rolling-type of apparatus that connects to the exterior of the skirt member 112 and moves within a track assembly mounted to the sidewall 107.

The vessel 105 may include a circular vertical sidewall 107 that is configured as a cylinder. Other configurations for the vessel are also within the scope of this disclosure. For instance, the vessel may be configured as a polygon with a plurality of planar walls. The examples discussed herein utilize sludge as an example of a gas-generating material contained within the vessel, but it is to be appreciated that any material that generates gas may be stored or otherwise placed in the vessel. For instance, any material suitable for anaerobic digestion may be introduced to the vessel 105, including wastewater from agricultural, municipal, and industrial processes, as well as waste such as microorganisms, biomass, biological waste, slurries, etc.

The floating cover described herein offers many advantages over floating covers that do not include the trough form frame structure. The floating cover of the subject invention provides additional rigidity to the cover structure, reduces costs by removing the need to build temporary preforms for forming the ballast material, and increases contractor safety by eliminating the need to do a blind lift operation of ballast material into the digester tank. The continuous ring configuration for the ballast structure also prevents the chance of loose blocks falling into the digester tank and damaging its internal structure.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A method of forming a cover of a sludge digester, the sludge digester having a vessel with an interior volume, the method comprising:
constructing a series of frame structure sections, each section including an outer wall and an inner wall spaced apart from the outer wall, the outer wall and the inner wall extending vertically from a horizontal base portion to form a trough member; and
joining the series of frame structure sections to each other to form a continuous ring, the continuous ring forming a perimeter of the cover and sized to fit within an inner diameter of the vessel.

2. The method of claim 1, further comprising filling at least a portion of the trough member with ballast material to form a continuous solid ring.

3. The method of claim 2, wherein filling is performed inside the interior volume of the vessel.

4. The method of claim 1, wherein constructing each section includes attaching the horizontal base portion to the outer wall.

5. The method of claim 1, wherein the outer wall is constructed to extend vertically above the inner wall and the method further comprises attaching a roof structure to an upper portion of the outer wall.

* * * * *